United States Patent [19]

Psilogenis

[11] Patent Number: 5,760,086
[45] Date of Patent: Jun. 2, 1998

[54] NASAL ADMINISTRATION OF AGENTS FOR TREATMENT OF DELAYED ONSET EMESIS

[75] Inventor: Mary Psilogenis, Tavernerio, Italy

[73] Assignee: RiboGene, Inc., Hayward, Calif.

[21] Appl. No.: 616,121

[22] Filed: Mar. 14, 1996

[51] Int. Cl.$^6$ .................................................. A61K 31/165
[52] U.S. Cl. ........................... 514/619; 514/965; 424/400
[58] Field of Search ..................................... 514/619, 965; 424/400

[56] References Cited

U.S. PATENT DOCUMENTS

4,624,965  11/1986  Wenig .......................................... 514/619

OTHER PUBLICATIONS

Clark et al., 1986, "Antiemetic (AE) trials to control delayed vomiting (V) following high–dose cisplatin (DDP)", *Proceedings of ASCO* 5:257, abstr. 1005.

Clark & Gralla, 1993, "Delayed emesis: A dilemma in antiemetic control", *Support Care Cancer* 1:182–185.

Cubeddu et al., 1993, "Participation of serotonin on early and delayed emesis induced by initial and subsequent cycles of cisplatinum–based chemotherapy: Effects of antiemetics", *J. Clin. Pharmacol.* 33:691–697.

De Mulder et al., 1990, "Ondansetron compared with high–dose metoclopramide in prophylaxis of acute and delayed cisplatin–induced nausea and vomiting", *Ann. of Internal Med.* 113:834–840.

Du Bois et al., 1995, "Cisplatin–induced alterations of serotonin metabolism in patients with or without emesis following chemotherapy", *Oncol. Rep.* 2:839–842.

D.R. Gandara, 1991, "Progress in the control of acute and delayed emesis induced by cisplatin", *Eur. J. Cancer* 27:S9–S11.

Gandera et al., 1992, "The delayed–emesis syndrome from cisplatin: Phase III evaluation of ondansetron versus placebo", *Semin. Oncol.* 19:67–71.

Grunberg et al., 1988, "Oral metoclopramide with or without diphenhydramine: Potential for prevention of late nausea and vomiting induced by cisplatin", *J. of the Natl. Can. Inst.* 80:864–868.

Jones et al., 1991, "Comparison of dexamethasone and ondansetron in the prophylaxis of emesis induced by moderately emetogenic chemotherapy", *Lancet* 338:483–486.

Kris et al., 1989, "Controlling delayed vomiting: Double-blind, randomized trial comparing placebo, dexamethasone alone, and metoclopramide plus dexamethasone in patients receiving cisplatin", *J. of Clin. Oncol.* 7:108–114.

Kris et al., 1992, "Oral ondansetron for the control of delayed emesis after cisplatin", *Cancer Suppl.* 70:1012–1016.

Lee et al., 1994, "Ondansetron compared with ondansetron plus metoclopramide in the prevention of cisplatin–induced emesis", *J. of Korean Med. Sci.* 9:369–375.

Levitt et al., 1993, "Ondansetron compared with dexamethasone and metoclopramide as antiemetics in the chemotherapy of breast cancer with cyclophosphamide, methotrexate, and fluorouracil", *New England J. of Med.* 328:1081–1084.

Li et al., 1991, "Control of cisplatin–induced delayed emesis", *Chin. Med. J. (Taipei)* 48:451–455.

Madej et al., 1994, "A report comparing the use of tropisetron (Navoban), a 5-$HT_3$ antagonist, with a standard antiemetic regimen of dexamethasone and metoclopramide in cisplatin–treated patients under conditions of severe emesis", *Semin. Oncol.* 21:3–6.

Moreno et al., 1992, "Comparison of three protracted antiemetic regimens for the control of delayed emesis in cisplatin–treated patients", *Eur. J. Cancer* 28:1344–1347.

Navari et al., 1995, "Oral ondansetron for the control of cisplatin–induced delayed emesis: A large, multicenter, double–blind, randomized comparative trial of ondansetron versus placebo", *J. of Clin. Oncol.* 13:2408–2416.

Nino et al., 1987, "A randomized controlled trial of acute and delayed cisplatin–induced emesis with metoclopramide, dexamethasone and prochlorperazine", *Jpn. J. Cancer Chemotgher.* 14:2881–2884.

O'Brien et al., 1989, "The role of metoclopramide in acute and delayed chemotherapy induced emesis: A randomized double blind trial", *Br. J. Cancer* 60:759–763.

G.S. Ogawa, 1982, "Metoclopramide as an antiemetic in chemotherapy", *New Eng. J. of Med. Correspond.* 307:249–250.

Roila et al., 1991, "Predictive factors of delayed emesis in cisplatin–treated patients and antiemetic activity and tolerability of metoclopramide or dexamethasone", *Am. J. Clin. Oncol. (CCT)* 14:238–242.

Scaglione et al., 1993, "Pharmacokinetics and bioavailability of metoclopramide nasal spray versus metoclopramide intravenous in healthy volunteers and cancer patients", *Arzneim.–Forsch.Drug Res.* 43:986–988.

Soukop et al., 1992, "Ondansetron compared with metoclopramide in the control of emesis and quality of life during repeated chemotherapy for breast cancer", *Oncol.* 49:295–304.

strum et al., 1985, "Management of cisplatin(DDP)–induced delayed–onset nausea(N) and vomiting(V): Preliminary results with 2 drug regimens", *Proceedings of ASCO* 4:263, abstr. C–1024.

M.C. Locatelli et al., Mar. 14, 1995, "Tolerability and Safety of Nasally Administered Metoclopramide (MCP) for the Prevention of CIS–Platinum (CDDP) Induced Delayed Emesis", *Proceedings of ASCO* vol. 14 Mar. 1995, abstr. 1759.

Chiara et al., 1995, "Prevention of Delayed Emesis with Metoclopramide and Dexamethasone in Patients Receiving Moderately Emetogenic Cytotoxic Treatment," *Anticancer Research* 15:1597–1599.

Tomirotti et al., 1994, "Efficacy and tolerability of nasally administered compared to parenterally administered metoclopramide in the symptomatic treatment of chemotherapy––induced emesis in cancer outpatients," *Support Care Cancer* 2:389–392.

Roila et al., 1994, "Cisplatin–induced delayed emesis: Pattern and prognostic factors during three subsequent cycles," *Annals of Oncology* 5:585–589.

*Primary Examiner*—James H. Reamer
*Attorney, Agent, or Firm*—Pennie & Edmonds LLP

[57] ABSTRACT

The present invention is directed to a method for the prophylactic management of delayed emesis by the use of metoclopramide nasal spray.

20 Claims, No Drawings

NASAL ADMINISTRATION OF AGENTS FOR TREATMENT OF DELAYED ONSET EMESIS

BACKGROUND OF THE INVENTION

1. Field of the Invention

The present invention is directed to a method for treating an emetogenic reaction. More particularly, the present invention is directed to a method for treating a delayed onset emetogenic reaction, most typically associated with chemotherapy.

2. Description of the Related Art

Emetogenic reaction refers to vomiting (i.e. actual vomiting or dry heaving or dry retching) and/or to nausea. The emetogenic reaction is most commonly encountered in response to chemotherapeutic agents such as bleomycin, vincristine, vinblastine, adriamycin, etoposide, methotrexate, doxorubicin, cyclophosphamide, ·5-fluorouracil, cisplatin and some combinations thereof. Among these chemotherapeutic agents, the most severe emetogenic reaction is usually associated with cisplatin therapy.

Generally, there are acute onset emetogenic reactions (hereinafter synonymous with "acute emesis" or "acute onset emesis") and delayed onset emetogenic reactions (hereinafter synonymous with "delayed emesis" or "delayed onset emesis"). Acute emesis and delayed emesis typically include vomiting episodes (actual and/or dry heaving or dry retching) and/or feelings of nausea. However, in acute emesis, the vomiting and/or nausea occur within the first 24 hours after chemotherapy. By contrast, in delayed emesis, the vomiting and/or nausea occur after the first 24 hours of chemotherapy. Delayed emesis is a distinct syndrome from acute emesis occurring more than 24 hours after the administration of anticancer agents, especially, cisplatin.

In a study by Kris et al. entitled Controlling Delayed Vomiting: Double-Blind, Randomized Trial Comparing Placebo, Dexamethasone Alone, and Metoclopramide Plus Dexamethosone in Patients Receiving Cisplatin published in the *Journal of Clinical Oncology*, Vol. 7, No. 1, at pp. 108-114 (January 1989), the authors report that delayed vomiting was observed in a 4 day period post cisplatin therapy (at a dosage level of 120mg/m² of body surface area) in 74% of patients and that delayed nausea was observed in 87% of the same patients over the same 4-day post cisplatin period. Kris et al. further reported that the severity and incidence of delayed emesis was most prevalent (i.e. worst) during the period of 48-72 hours (i.e. days 2-3 post cisplatin administration) after cisplatin therapy was given. Further, according to Kris et al.

As the control of acute emesis following high doses of cisplatin has improved, the need to address the remaining problem of delayed nausea and vomiting [i.e. delayed emesis] beginning or persisting for more than 24 hours after cisplatin has become apparent. (Emphasis added.) Id at p. 113.

The patients in the Kris et al. study received a two drug regimen of oral dexamethasone (i.e. DXM po) and oral metoclopramide (i.e. MCP po). Side effects observed in the Kris et al. study patients included hiccoughs, loose bowel movements (LBMs), heartburn, restlessness, sleepiness, insomnia and acute dystonic reactions. Among these symptoms, restlessness and sleepiness were the most common.

In another study, the side effects of oral MCP for the prophylaxis of delayed emesis (i.e. delayed nausea and/or vomiting) induced by cisplatin were reported by Grunberg et al., in Oral Metoclopramide With or Without Diphenhydramine: Potential for Prevention of Late Nausea and Vomiting Induced by Cisplatin, published in the *Journal of the National Cancer Institute*, Vol. 80, No. 11, pp. 864–868 (Aug. 3, 1988). The most severe toxic effects observed were extrapyramidal symptoms, agitation and depression.

Side effects may interfere with patient compliance (compliance=following dosage regimen prescribed) with the drug regimen prescribed as well as interfere with the patient's ability to effectively communicate the nature and severity of this and other side effects. Even with a short-term medication regimen, poor compliance or non-compliance is observed in about 25% of patients.

Additionally, oral therapy may be unsuitable for some patients experiencing a delayed emetogenic reaction. Due to nausea and/or vomiting, the patient may be even more reluctant to comply with the oral drug regimen. Therefore, there is a need to provide treatment or prophylaxis (i.e. complete or partial prophylaxis) for delayed emesis in an appropriate dosage form wherein the problems associated with non-compliance (e.g. with oral or intravenous dosage forms) are avoided.

U.S. Pat. No. 4,624,965 (hereinafter Wenig) discusses nasal administration of MCP. In Wenig, at column 1, lines 40–52, it is stated that A number of antinausea and antiemetic agents are already known. Such agents are widely used therapeutically, chiefly in the treatment of emesis and nausea . . . Unfortunately, many of these agents when used: (1) cause undesirable side effects, (2) are inefficiently and variably absorbed from current dosage forms, (3) are difficult or inconvenient to administer in the current dosage forms [e.g. oral, intravenous, intramuscular or subcutaneous dosage forms] . . . (Emphasis added.)

Further, in Examples 8 and 9 of Wenig (See columns 11 and 12 therein), human subjects are studied. However, a gel intranasal formulation is used as opposed to a nasal spray. No experience with human subjects using a nasal spray formulation of MCP (MCP ns) is disclosed within Wenig.

Since chronic or severe nausea and/or vomiting can significantly influence a patient's ability to maintain an acceptable level of health, for example, after chemotherapy, it is desirable to provide a method for treating and sufficiently controlling (prophylactically controlling) such emetogenic reactions. In the case of chemotherapy-induced delayed emesis, the control and treatment of the nausea and/or vomiting can not only help to maintain an acceptable level of health but can also aid in maintaining an aggressive cancer treatment program.

To that end, while advances have been made in the area of controlling and treating acute emesis, treatment for adequate control of delayed emesis was heretofore not available.

SUMMARY OF THE INVENTION

It is therefore an object of the present invention to provide a method for treating delayed emesis by using a dosage form of MCP that avoids or reduces the incidence of patient non-compliance.

It is therefore another object of the present invention to provide a method for treating delayed emesis by using MCP nasal spray that avoids or reduces the incidence of side-effects experienced by patients.

It is therefore yet another object of the present invention to provide a method for treating delayed emesis by using MCP nasal spray administered intranasally.

3

It the therefore even yet another object of the present invention to provide a method for treating delayed emesis induced by chemotherapy by using a dosage form of MCP that avoids or reduces the problem of patient non-compliance.

It is still another object of the present invention to provide a method for treating delayed emesis induced by cisplatin chemotherapy by using a dosage form of MCP that avoids or reduces the problem of patient non-compliance.

It is yet still another object of the present invention to provide a method for sufficiently treating delayed emesis induced by chemotherapy using a dosage form of MCP that avoids or reduces the incidence of side-effects experienced by patients.

It is even yet still another object of the present invention to provide a method for sufficiently treating delayed emesis induced by cisplatin chemotherapy using MCP nasal spray that avoids or reduces the severity of side-effects experienced by patients.

It is a further object of the present invention to provide a method for controlling delayed emesis induced by chemotherapy using MCP nasal spray administered intranasally after the first 24 hours of completing chemotherapy.

It is an even further object of the present invention to provide a method for sufficiently controlling delayed emesis induced by cisplatin chemotherapy using MCP nasal spray that avoids or reduces the problems associated with patient non-compliance.

It is an even yet further object of the present invention to provide a method for prophylaxis of delayed emesis by intranasally administering a pharmaceutically acceptable MCP nasal spray dosage form at a therapeutic dosage level of between about 1.95 mg/kg to about 3.9 mg/kg on days 1–7 wherein chemotherapy was administered on day 0.

It is still another object of the present invention to provide a method for prophylaxis of delayed emesis by intranasally administering a pharmaceutically acceptable MCP nasal spray dosage form at a therapeutic dosage level of between about 1.95 mg/kg to about 3.9 mg/kg on days 1–6 wherein cisplatin was administered.

It is still another object of the present invention to provide a method for prophylaxis of delayed emesis by intranasally administering a pharmaceutically acceptable MCP nasal spray dosage form at a therapeutic dosage level of between about 0.8 mg/kg to about 1.0 mg/kg on days 1–5 wherein cisplatin was administered.

It is still another object of the present invention to provide a method for prophylaxis of delayed emesis by intranasally administering a pharmaceutically acceptable MCP nasal spray dosage form at a therapeutic dosage level of between about 0.9 mg/kg to about 1.1 mg/kg on days 1–4 wherein cisplatin was administered.

It is still another object of the present invention to provide a method for prophylaxis of delayed emesis by intranasally administering a pharmaceutically acceptable MCP nasal spray at a therapeutic dosage level of between about 40 mg/day–120 mg/day on days 1–7 wherein chemotherapy was administered by 0.

It is still another object of the present invention to provide a method for prophylaxis of delayed emesis by intranasally administering a pharmaceutically acceptable MCP nasal spray at a therapeutic dosage level of between about 40 mg/day–120 mg/day on days 1–6 wherein cisplatin was administered on day 0.

It is still another object of the present invention to provide a method for prophylaxis of delayed emesis by intranasally administering a pharmaceutically acceptable MCP nasal spray at a therapeutic dosage level of about 60 mg/day on days 1–6 wherein chemotherapy was administered on day 0.

It is still another object of the present invention to provide a method for prophylaxis of delayed emesis by intranasally administering a pharmaceutically acceptable MCP nasal spray at a therapeutic dosage level of about 60 mg/day on days 1–6 wherein cisplatin was administered on day 0.

It is still another object of the present invention to provide a method for prophylaxis of delayed emesis by intranasally administering a pharmaceutically acceptable MCP nasal spray at a therapeutic dosage level of about 60 mg/day on days 1–5 wherein cisplatin was administered on day 0.

It is still another object of the present invention to provide a method for prophylaxis of delayed emesis by intranasally administering a pharmaceutically acceptable MCP nasal spray at a therapeutic dosage level of about 60 mg/day on days 1–4 wherein cisplatin was administered on day 0.

These and other objects of the present invention are accomplished by administering intranasally to patients experiencing delayed emesis a therapeutically effective dosage of MCP nasal spray in a pharmaceutically acceptable dosage form which is therapeutically and medically acceptable.

DETAILED DESCRIPTION OF THE PREFERRED EMBODIMENTS

The presently disclosed invention is directed to a method for treating and controlling delayed emesis by using a MCP nasal spray dosage formulation. The MCP nasal spray dosage form is formulated to contain a therapeutically effective amount of MCP such that upon administration by the intranasal route, a therapeutically effective amount of MCP is delivered to the patient. In addition, the therapeutically effective amount of MCP is chosen to minimize the severity and incidence of untoward side-effects and drug-interactions encountered with MCP.

The MCP nasal spray formulation administered to deliver a dose of 20 mg three times a day is indicated below (formulation per 0.1 ml of MCP nasal spray (MCP ns=metoclopramide nasal spray dosage form)):

| | |
|---|---|
| 10 mg/0.1 ml | metoclopramide hydrochloride |
| 1.5 mg | benzyl alcohol |
| 0.8 mg | NaCl |
| 0.320 mg | glacial acetic acid |
| 0.077 mg | sodium acetate |
| 6.425 mg | sorbitol |
| 0.1 ml | purified water (qs ad to 0.1 ml). |

The MCP nasal spray formulation was given (to the patients indicated in FIGS. 1(a) and 1(b)) as 1 puff per nostril (i.e. 2 puffs at 10 mg/puff (10 mg/0.1 ml and 0.1 ml/puff)) three times a day (2 puffs TID for 6 days). The above formulation was sterile with a bacteria count of 10 below the level allowed by the U.S.P. on a per ml basis. In addition, pathogens were absent. The pH of the above formulation was about 4.0.

Typical MCP nasal spray dosage forms are solutions or suspensions that can be administered as a nasal spray. However, nasal drops may also be used. The MCP nasal spray dosage formulation contains the active agent in any suitable form e.g. salt, as the hydrochloride etc. The MCP nasal spray dosage formulation typically also contains pH adjusters, emulsifiers or dispersing agents, buffering agents, preservatives and wetting agents as are known to those skilled in the art. See REMINGTON'S PHARMACEUTI- CAL SCIENCES, 14th Edition, 1970. Typically, the MCP nasal spray dosage formulation is isotonic.

A typical MCP nasal spray formulation is in solution form having a light amber color and being non-cloudy to the naked eye with an pH of between about 3.0–5.0. The typical formulation may contain benzyl alcohol of at least about 13.5 mg/ml containing practically no impurities as determined by high pressure liquid chromatography (HPLC) and having a bacterial count of less than 250 ufc/ml and free of pathogens sufficient to form an acceptable pharmaceutical nasal spray dosage form. The solvent is typically purified water suitable for use in nasal spray dosage forms or any equivalent water (e.g. injectable water) that is allowed for use in such nasal dosage forms. See REMINGTON'S PHARMACEUTICAL SCIENCES, any edition from 1980–1996. For the adequate and/or sufficient treatment and control of delayed emesis (e.g. chemotherapy induced, cisplatin induced or induced by other causes), a typical dose is that dose which is therapeutically effective and which minimizes side-effects and drug interactions, for example, in patients receiving chemotherapy.

A typical dosage of MCP nasal spray for the treatment and control of delayed onset emesis depends upon the degree and severity of delayed emesis experienced by a typical patient (e.g. chemotherapy induced delayed emesis). The dosage of MCP nasal spray may be varied between about 40 mg/day to about 120 mg/day. Above about 120 mg/day, the dosage may be undesirable due to untoward side effects experienced by patients receiving more than about 120 mg/day from the MCP nasal spray dosage form. A preferred dosage of MCP nasal spray is 60 mg/day typically given as 20mg three times a day (i.e. 2 puffs of 10 mg/0.1 ml of MCP nasal spray, one puff per nostril).

The weight of the patient may also affect the dosage to be administered. Typically, a dose of between about 1.95 mg/kg to about 3.90 mg/kg is given to an patient experiencing delayed emesis (e.g. chemotherapy induced delayed emesis). A preferred dosage is about 0.8 mg/kg.

The aforementioned dosages for the treatment and control of delayed emesis are given after 24 hours from the time that the chemotherapeutic regimen cycle has been administered. Thus, for example, if the chemotherapeutic regimen cycle is given between 2:00 to 4:00 pm on day zero, then the MCP nasal spray is administered starting at about 4:00 pm on day 1–day 7, typically, in three or four equal dosages at three or four equal time intervals, respectively. However, the dosage may be given during waking hours so as not to wake the patient. Note that the MCP nasal spray dosage form is administered intranasally and is given in addition to medications administered for the treatment and control of acute emesis. All references cited within this patent application are incorporated herein by reference in their entirety and for all purposes.

Having described the invention, the following examples are included to illustrate the benefits of the present invention. The examples are only illustrative and are not meant to unduly limit the scope of the present invention.

EXAMPLES

Example 1

Table I indicates the characteristics of patients that received metoclopramide nasal spray alone or metoclopramide nasal spray (MCP ns) and dexamethasone (DXM) for controlling delayed emeses induced by chemotherapy. Primary disease site indicates primary location of cancer.

TABLE I

| PATIENTS' CHARACTERISTICS | |
|---|---|
| Number of patients | 12 |
| Sex | |
| Male | 2 |
| Female | 10 |
| Age (years) | |
| Mean | 50 |
| Range | 23–63 |
| Primary disease site | |
| Ovary | 8 patients |
| Testis | 1 patient |
| Bladder | 3 patients |

Table II indicates the chemotherapy regimen that each of the patients received on day 0.

TABLE II

| CHEMOTHERAPY REGIMEN (administered on day 0) | |
|---|---|
| Cisplatin | 1 patient |
| Cisplatin + Cyclophosphamide | 5 patients |
| Cisplatin + Cyclophosphamide + Adriamycin | 3 patients |
| Cisplatin + Cyclophosphamide + Vinblastine + Methotrexate | 2 patients |
| Cisplatin + Etoposide + Bleomycin | 1 patient |

Example 2

Table III indicates the vomiting, retching and nausea reported in each patient during days 1 through 6 following chemotherapy on day 0. Note that MCP nasal spray (60 mg/day) indicates administration of a MCP nasal spray formulation per 0.1 ml of:

| 10 mg/0.1 ml | metoclopramide hydrochloride |
|---|---|
| 1.5 mg | benzyl alcohol |
| 0.8 mg | NaCl |
| 0.320 mg | glacial acetic acid |
| 0.077 mg | sodium acetate |
| 6.425 mg | sorbitol |
| 0.1 ml | purified water (qs to 0.1 ml). |

The MCP nasal spray formulation was given as 1 puff per nostril (i.e. 2 puffs at 10 mg/puff (10 mg/0.1 ml and 0.1 ml/puff)) three times a day (2 puffs TID for 6 days). The above formulation was sterile for bacteria. In addition, pathogens were absent. The pH of the above formulation was about 4.0.

TABLE III

VOMITING, RETCHING AND NAUSEA REPORTED IN EACH PATIENT DURING DAYS 1 THROUGH 6 FOLLOWING CHEMOTHERAPY (Chemotherapy administered on day 0)

| TREATMENT | PATIENT NO. | VOMITING No. of emetic episodes/day DAY | | | | | | RETCHING No. of episodes/day DAY | | | | | | NAUSEA Intensity*/day DAY | | | | | |
|---|---|---|---|---|---|---|---|---|---|---|---|---|---|---|---|---|---|---|---|
| | | 1 | 2 | 3 | 4 | 5 | 6 | 1 | 2 | 3 | 4 | 5 | 6 | 1 | 2 | 3 | 4 | 5 | 6 |
| MCP ns | 1 | 0 | 3 | 0 | 0 | 0 | 0 | 0 | 1 | 1 | 0 | 0 | 0 | 1 | 2 | 2 | 1 | 1 | 0 |
| (60 mg/day) | 3 | 0 | 0 | 0 | 0 | 0 | 0 | 0 | 0 | 0 | 0 | 0 | 0 | 3 | 2 | 3 | 3 | 2 | 2 |
| | 4 | 0 | 1 | 0 | 0 | 0 | 0 | 0 | 1 | 0 | 0 | 0 | 0 | 0 | 0 | 0 | 0 | 0 | 0 |
| | 5 | 0 | 6 | 3 | 4 | 2 | 0 | 0 | 0 | 0 | 0 | 0 | 0 | 0 | 2 | 2 | 2 | 2 | 2 |
| | 6 | 0 | 1 | 4 | 0 | 0 | 0 | 0 | 0 | 0 | 0 | 0 | 0 | 0 | 0 | 1 | 1 | 1 | 1 |
| MCP ns | 7 | 10 | 10 | 9 | 10 | 10 | 10 | 0 | 0 | 0 | 0 | 0 | 0 | 3 | 3 | 3 | 3 | 2 | 2 |
| (60 mg/day) + | 8 | 0 | 0 | 0 | 1 | 0 | 0 | 0 | 0 | 0 | 0 | 0 | 0 | 1 | 1 | 1 | 3 | 1 | 1 |
| DXM | 9 | 2 | 3 | 1 | 0 | 0 | 0 | 0 | 0 | 0 | 0 | 0 | 0 | 2 | 2 | 2 | 2 | 1 | 1 |
| (8 mg/day) | 10 | 2 | 3 | 3 | 4 | 3 | 2 | 0 | 1 | 2 | 0 | 0 | 0 | 1 | 1 | 2 | 2 | 3 | 3 |
| | 11 | 0 | 1 | 0 | 0 | 0 | 0 | 0 | 0 | 0 | 0 | 0 | 0 | 1 | 1 | 1 | 0 | 0 | 0 |
| | 12 | 0 | 0 | 0 | 0 | 0 | 0 | 0 | 0 | 0 | 0 | 0 | 0 | 1 | 1 | 0 | 0 | 0 | 0 |

*1 = mild,
2 = moderate,
3 = severe
Patient No. 2 was not included because he received fractionation of chemotherapy, he was treated with MCP ns and he had no vomiting retching or nausea (complete response)

Example 3

The results of MCP nasal spray therapy (given on day 1–6) for the treatment and control (partial or complete prophylaxis) of delayed emesis is indicated in Table IV.

TABLE IV(a)

| COMPLETE RESPONSE (no emetic episodes) BY STUDY DAY | | |
|---|---|---|
| COMPLETE RESPONSE† DAY | MCP ns number of patients | MCP ns + DXM number of patients |
| 1 | 5/5 | 3/6 |
| 2 | 1/5 | 2/6 |
| 3 | 3/5 | 3/6 |
| 4 | 4/5 | 3/6 |
| 5* | 8/11 | — |
| 6* | 9/11 | — |

Thus, on day 1 all 5 of 5 patients that received MCP ns had no emetic episodes (complete response) while only 3 of 6 patients that received MCP ns+DXM showed no emetic episodes.

TABLE IV(b)

| MAJOR RESPONSE (1–2 emetic episodes) | | |
|---|---|---|
| MAJOR RESPONSE‡ DAY | MCP ns number of patients | MCP ns + DXM number of patients |
| 1 | — | 2/6 |
| 2 | 2/5 | 1/6 |
| 3 | — | 1/6 |
| 4 | — | 1/6 |
| 5* | 1/11 | — |
| 6* | 1/11 | — |

† = complete response = 0 emetic episodes
‡ = major response = 1–2 emetic episodes
* = on days 5 and 6 all patients received only MCP ns (60 mg/day); and — = 0.

Similarly on day 1, no patients that received MCP ns had any emetic episodes (major response) while 2 of 6 patients who received MCP ns+DXM had 1–2 emetic episodes.

What is claimed is:

1. A method for prophylaxis of delayed emesis comprising the step of:
    administering a pharmaceutically acceptable metoclopramide nasal spray formulation via an intranasal route to deliver a therapeutically effective and medically acceptable daily dosage for said prophylaxis.

2. The process of claim 1 wherein said daily dosage is between about 40 mg/day to about 120 mg/day.

3. The process of claim 2 wherein said daily dosage is between 40 mg/day to 120 mg/day.

4. The process of claim 2 wherein said daily dosage is about 60 mg/day.

5. The process of claim 4 wherein said daily dosage is 60 mg/day.

6. The process of claim 1 wherein said daily dosage is divided into 3 or 4 equal smaller doses and administered at equally spaced intervals within 24 hours.

7. The process of claim 6 wherein said smaller doses are 20 mg and administered every 8 hours.

8. The process of claim 1 wherein said daily dosage is between about 1.95 mg/kg to about 3.90 mg/kg.

9. The process of claim 8 wherein said daily dosage is between 1.95 mg/kg to 3.90 mg/kg.

10. The process of claim 9, wherein said daily dosage is about 0.8 mg/kg.

11. The process of claim 10 wherein said daily dosage is 0.8 mg/kg.

12. The process of claim 11 wherein said daily dosage is divided into 3 or 4 equal smaller doses and administered at equally spaced intervals within 24 hours.

13. The process of claim 12 wherein said daily dosage is divided into 3 equal smaller doses and administered at equally spaced intervals within 24 hours.

14. The process of claim 12 wherein daily dosage is divided into 4 equal smaller doses and administered at equally spaced intervals within 24 hours.

15. The process of claim 1 wherein said dosage is administered for prophylaxis of delayed emesis induced by chemotherapy.

16. The process of claim 15 wherein said dosage is induced by chemotherapeutic agents selected from the group consisting of cisplatin, cyclophosphamide, adriamycin, vinblastine, methotrexate, etoposide, bleomycin, vincristine and combinations thereof.

17. The process of claim 16 wherein said daily dosage is administered during 24–168 hours after completion of said chemotherapy.

18. The process of claim 16 wherein said daily dosage is administered during 24–144 hours after completion of said chemotherapy.

19. The process of claim 16 wherein said daily dosage is administered during 24–120 hours after completion of said chemotherapy.

20. The process of claim 16 wherein said daily dosage is administered during 24–96 hours after completion of said chemotherapy.

* * * * *